(12) United States Patent
Bakarania et al.

(10) Patent No.: US 8,652,037 B2
(45) Date of Patent: Feb. 18, 2014

(54) DATA COLLECTION SYSTEM AND INTERFACE

(75) Inventors: Neel Bakarania, Brighton, MA (US); Joseph Flaherty, Westford, MA (US); Timothy Golnik, Boxford, MA (US); Robert F. Rice, Quincy, MA (US); Gary Tsai, Cambridge, MA (US); Sonny Vu, Salem, NH (US); Baoguo Wei, Salem, NH (US)

(73) Assignee: AgaMatrix, LLC, Salem, NH (US)

( * ) Notice: Subject to any disclaimer, the term of this patent is extended or adjusted under 35 U.S.C. 154(b) by 1905 days.

(21) Appl. No.: 11/423,093

(22) Filed: Jun. 8, 2006

(65) Prior Publication Data

US 2006/0279431 A1     Dec. 14, 2006

Related U.S. Application Data

(60) Provisional application No. 60/595,132, filed on Jun. 8, 2005, provisional application No. 60/596,344, filed on Sep. 18, 2005.

(51) Int. Cl.
*A61B 5/00*     (2006.01)

(52) U.S. Cl.
USPC ............................... 600/300; 340/870.07

(58) Field of Classification Search
USPC ............................................. 600/300
See application file for complete search history.

(56) References Cited

U.S. PATENT DOCUMENTS

| | | | |
|---|---|---|---|
| 4,370,983 A | 2/1983 | Lichtenstein | |
| 4,731,726 A | 3/1988 | Allen, III | |
| 5,019,974 A | 5/1991 | Beckers | |
| 5,615,672 A | 4/1997 | Braig et al. | |
| 5,900,632 A | 5/1999 | Sterling et al. | |
| 5,997,475 A | 12/1999 | Bortz | |
| 6,024,699 A | 2/2000 | Surwit et al. | |
| 6,085,752 A | 7/2000 | Kehr et al. | |
| 6,188,648 B1 | 2/2001 | Olsen | |
| 6,544,212 B2 | 4/2003 | Galley et al. | |
| 6,558,320 B1 * | 5/2003 | Causey et al. | 600/300 |
| 6,645,142 B2 | 11/2003 | Braig et al. | |

(Continued)

FOREIGN PATENT DOCUMENTS

WO     2005041432 A1     5/2005

*Primary Examiner* — Albert Wong
(74) *Attorney, Agent, or Firm* — Larson & Anderson, LLC (57) ABSTRACT

A data collection system is formed from an analyte detection meter and a base station. The meter and the base station are operatively connected to one another to transfer data from the meter. The base station is able to communicate transferred data to a data receiving server, and the transfer of data occurs in response to a defined stimulus such as the proximity of the meter and base station or an alarm set at a predetermined time of day. The data collection system can be used in combination with a system interface that provides a data management system (DMS) resident on a device such as a personal computer. The DMS can recognize a particular meter and may incorporate into the displayed information not only the data resident on the meter but also information previously transferred from the meter. The DMS may be launched on the computer as soon as connection with a meter is detected. The DMS may also reproduce the display of the particular meter on the display of the computer such that the user need only learn one set of controls. Changes to the setting of the meters may be accomplished through the computer and an update transferred and stored on the connected meter.

8 Claims, 8 Drawing Sheets

(56) References Cited

U.S. PATENT DOCUMENTS

| | | |
|---|---|---|
| 6,790,178 B1 | 9/2004 | Mault et al. |
| 6,936,007 B2 | 8/2005 | Quy |
| 6,968,375 B1 | 11/2005 | Brown |
| 7,025,425 B2 | 4/2006 | Kovatchev et al. |
| 7,041,468 B2 | 5/2006 | Drucker et al. |
| 7,077,328 B2 | 7/2006 | Krishnaswamy et al. |
| 7,103,578 B2 | 9/2006 | Beck et al. |
| 7,395,117 B2 * | 7/2008 | Mazar et al. .................... 607/60 |
| 2002/0135336 A1 | 9/2002 | Zhou et al. |
| 2003/0125074 A1 * | 7/2003 | Tanada et al. ................. 455/552 |
| 2003/0163622 A1 * | 8/2003 | Moran ............................ 710/74 |
| 2004/0015102 A1 | 1/2004 | Cummings et al. |
| 2004/0039255 A1 | 2/2004 | Simonsen et al. |
| 2004/0044272 A1 | 3/2004 | Moerman et al. |
| 2004/0243664 A1 * | 12/2004 | Horstemeyer ................ 709/200 |
| 2006/0064020 A1 * | 3/2006 | Burnes et al. ................. 600/481 |
| 2006/0258289 A1 * | 11/2006 | Dua ............................ 455/41.3 |
| 2007/0156033 A1 * | 7/2007 | Causey et al. ................ 600/300 |
| 2007/0293733 A1 * | 12/2007 | Quy ............................ 600/300 |

\* cited by examiner

DATA COLLECTION SYSTEM AND INTERFACE

BACKGROUND OF THE INVENTION

This application relates to a data collection system and interface that can be used to facilitate the transfer of data between a portable or hand-held blood glucose or similar analyte detection meter and a base station, and the communication of such information and the management of the meter by a user.

The vast majority of diabetics do not diligently measure and control their level of blood glucose. Even among diabetics who have glucose meters and test strips available to them, in the main, the majority are not diligent about measuring and controlling blood glucose, and do not keep consistent records about measurements of blood glucose.

Some past glucose meters have been designed with communications ports so that data can be downloaded from the meter to a personal computer. With such a meter/computer combination, it is intended that the computer will accumulate historical information and that this will assist the patient in tracking and controlling blood glucose levels. Experience has shown, however, that even with such systems, the success rate at getting patients to be consistent and diligent is very much an uphill struggle and only a disappointingly small percentage of such patients are diligent about this.

It would therefore be desirable to have a data collection system and interface that facilitates compliance by the patient with needs for testing and monitoring.

SUMMARY OF THE INVENTION

The present invention provides a data collection system and a data collection interface that can be used individually or together to enhance the compliance of individual users of analyte testing systems such as hand-held blood glucose meters.

In accordance with the data collection system of the invention, a protocol is established by which test result information stored in the hand-held meter is periodically and routinely transferred from the meter to a base station such as a personal computer. In some embodiments of the invention, this transfer is accomplished without user intervention. It is contemplated that the base station will have greater data storage and processing capacity, to allow determination and monitoring of test result trends and compliance, and communications capability that permit notification of appropriate third parties such as family members or health care providers where result trends or compliance fall outside acceptable limits.

Figure 1:
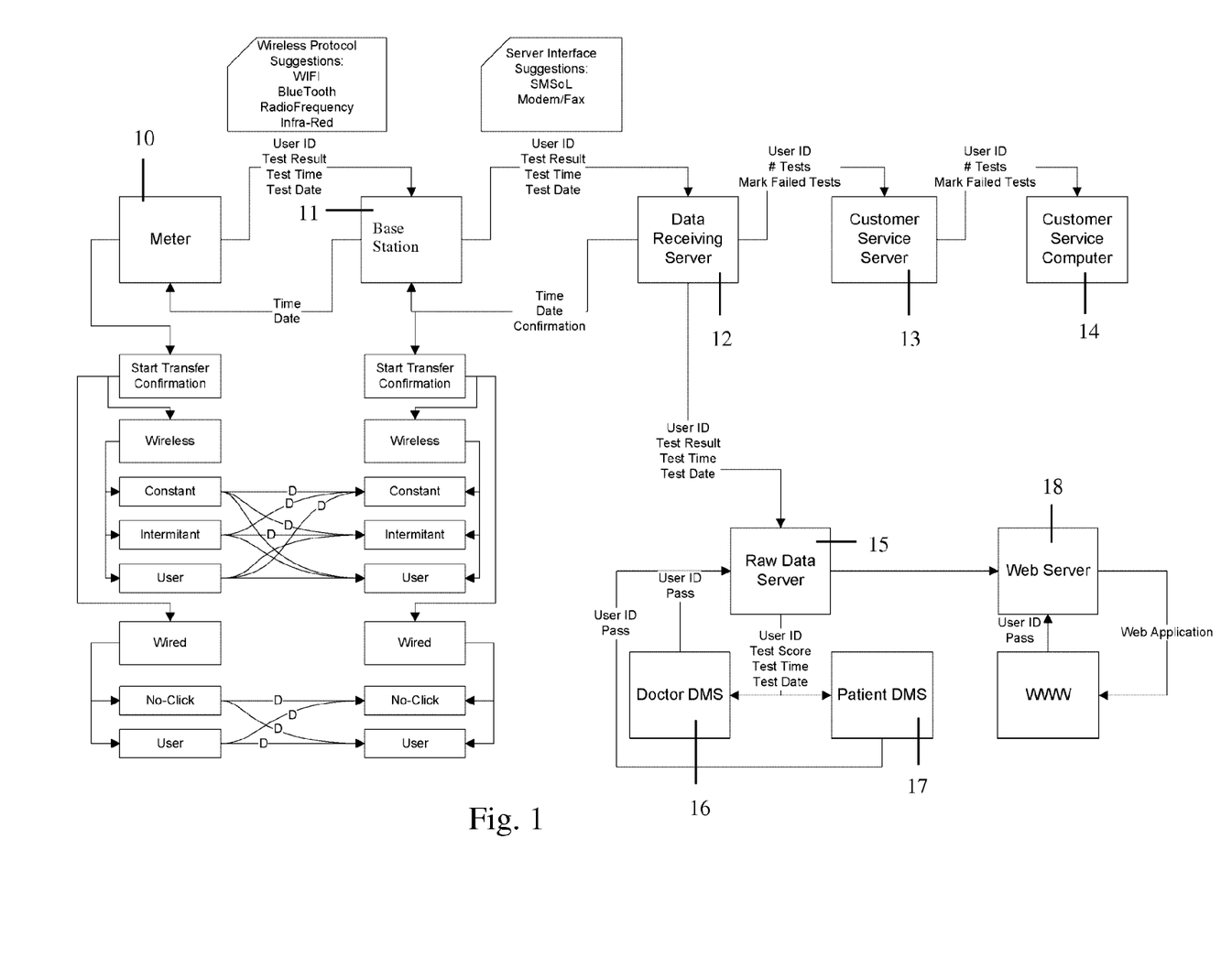
FIG. 1 shows exemplary data flow opportunities according to the data collection system of the invention.

The system interface of the invention provides a data management system resident on a computer (for example the data receiving server or the doctor or patient DMS on FIG. 1) that provides a display to the user of data obtained from a connected meter. In one embodiment, the data management system recognizes a particular meter connected to the computer and may incorporate into the displayed information not only the data resident on the meter but also information previously transferred from the meter. In one embodiment, the data management system is launched on the computer as soon as connection with a meter is detected. In a further embodiment, the interface reproduces the display of the particular meter on the display of the computer such that the user need only learn one set of controls. In a further embodiment, changes to the setting of the meters may be accomplished through the computer and DMS and an update transferred and stored on the connected meter.

DETAILED DESCRIPTION OF THE INVENTION

The data collection system and interface of the invention are particularly suited for use in combination with meters intended for monitoring of blood glucose levels, for example in an individual with diabetes. For this reason and for simplicity of presentation, the discussion that follows is couched in terms specific to glucose monitoring. The invention is not limited to applications where the analyte being monitored is glucose, however, and may be used without regard for the nature of the analyte that is being monitored.

Monitoring for blood glucose is commonly performed with a glucose meter used by a patient to measure a level of blood glucose. The user inserts a test strip into the meter. The user pricks the skin, releasing a drop of blood. The user touches the test strip to the drop of blood. The meter performs an analysis of the blood and determines a level of blood glucose. The result of the test is stored in the meter along with information about the time of day at which the test occurred and any other information provided by the patient, such as information as to how recently the patient ate a meal. Various types of meters for this purpose are known and can be used with the present invention, including without limitation those disclosed in U.S. application Ser. No. 10/907,790, filed Apr. 15, 2005, which application is incorporated herein by reference for all purposes, and currently commercially-available meters.

Data Collection System of the Invention

The data collection system of the invention comprises a meter for detection of an analyte such as glucose and a base station for receiving data from the meter. The base station can, at a minimum, interact with the meter to initiate the transfer of data from the meter. The base station further possesses the ability to transfer in the data to at least one data receiving server. Preferably, the system, through either the meter, the base station or both, conveys to the user when the data transfer is ongoing and when it has been successfully completed. In certain embodiments, the base station is a separate entity apart from the data receiving server, and has no capability to display information about the results to the user. In other embodiments, the base station is integrated with the data receiving server, such that it can both transmit and display information.

FIG. 1 shows exemplary data flow opportunities useful in the data collection system of the invention. It will be appreciated that the communications can be two-way, and that data can be transferred to the meter to the base station, and from the base station to the meter. The basic data collection system comprises the meter 10 and the base station 11 in communication with one another through a wired or wireless connection. Examples of suitable wireless protocols/hardware which serve as a means for communication therebetween include Wifi (e.g. 802.1'1b), Bluetooth, infrared, and other RF protocols. As compared with Bluetooth, Wifi draws more power but can go a greater distance. Bluetooth may be preferable due to its lower power requirements. Infrared can also be used, but it may require aligning the infrared port of the meter with the infrared port of the base station which may be difficult for some users.

FIG. 1 also shows types of information communicated between meter 10 and the base station 11. For example, the base station 11 can provide time and date information to the meter 10, thus correcting any clock/calendar drift). The meter provides more information to the base station, for example a user ID for a test, the test results, and the date and time of the test.

In columns below the meter 10 and the base station 11 are boxes showing ways in which communication therebetween may be initiated. These are discussed further below.

FIG. 1 also elaborates, in the upper right portion of the figure, upon uses to which the system may put the received test information. For example, data receiving server 12 may pass along to a customer service server 13 information as to the number of failed tests, the total number of tests, and the user ID. This would in turn be passed to a customer service computer 14. This permits a customer service person to monitor the status and to contact the user, for example, when it is time to reorder consumables such as test strips. The customer service person can also contact the user if there are too many failed tests. Communication between the base station 11 and the data receiving server 12 may be SMS over landline, or modem, in exemplary embodiments. The base station 11 will forward to the receiving center the information which it previously received from the meter. In return, the data receiving server 12 may provide up-to-date time and date information to the base station 11.

The data receiving server 12 can also monitor the circumstance where too much time passes without a test report. This can prompt a call or other communication to a relative or physician who can check on the user. The data receiving server 12 can also (as shown in the lower right portion of the figure) pass data to a raw data server 15, which can in turn pass data to a doctor database management system (DMS) 16 or a patient database management system 17, or both. Each requires at least a user ID and password for access. The raw data server can also pass data to a web server 18 which makes it available by means of a web application to a user.

In general, the data receiving server can thus pass on a variety of message, including without limitation (1) a message based on the number of tests done indicating that additional supplies may be needed by the user;

(2) a message that the number or frequency of tests performed is not in compliance with monitoring needs of the user, (3) a message that the numerical values of the test results is greater or less than a target value such that medial attention may be necessary, (4) a message communicating the number and nature of error codes, and (5) a message representing annotations to the results, such as the time of the last meal.

Although FIG. 1 depicts the base station and the various servers as individual components, it will be appreciated that some or all of these components can be combined within a single computer. For example, the base station 11 may serve the functions of the data receiving server, transmitting messages to customer service or a physician or family as appropriate.

Figure 2A:
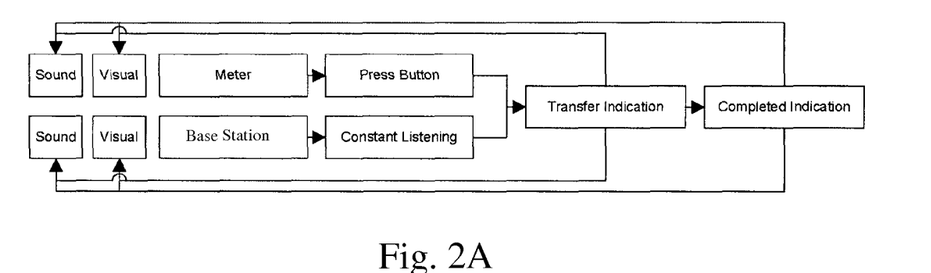
FIGS. 2A and B depict a sequence of steps using the pressing of a button on a meter to initiate the data collection system of the invention.
Figure 2B:
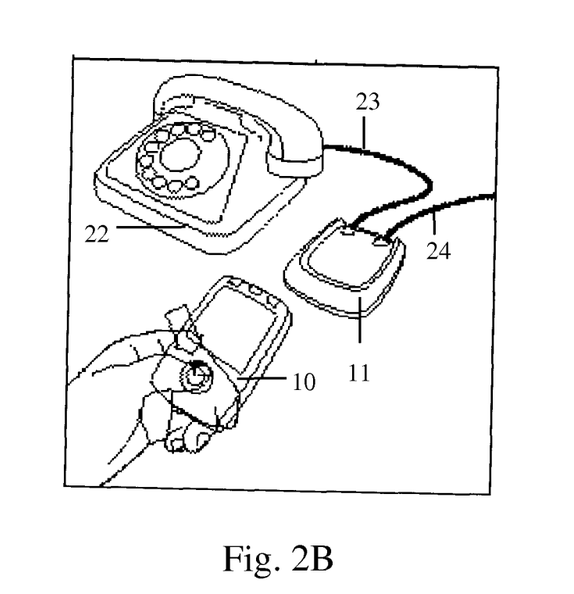

FIGS. 2A and B depict one method by which communication between the meter 10 and the base station 11 may be initiated. In this embodiment, transfer of information is initiated by pressing a button on the meter 10. The base station 11 listens constantly for a wireless signal from the meter. Eventually the user presses a button on the meter. This prompts the meter to transmit a signal to the base station. This signal causes the base station and meter to establish a connection, for example a wireless connection. The base station collects information from the meter. An indication, audio or visual or both, is provided to let the user know that the information transfer is taking place.

FIG. 2B shows an implementation of this approach using a telephone 22 connected to base station 11 via wire 23 which is in turn connected to a data receiving server, not shown, via wire 24 that connects to a phone jack. In this embodiment, the base station 11 lies between the telephone 22 and the telephone jack (not shown). Such an installation is rather like installing a Caller ID box or an answering machine. The mode of communications between the base station and the remote host is preferably SMS (short message service) over landline. This mode communicates short messages (typically limited to 160 characters) by a modulation that does not interfere with voice communications (e.g. the typical 1200 bits-per-second modulation also used for caller ID). Another possible mode is modem communications. A 300-baud modem is more than adequate for the purposes described herein, and is inexpensive. Faster modems could also be used, such as 9600-bits-per-second or faster speeds. The use of a modem has the potential drawback that it will not work while a voice call is taking place. On the other hand, the modem can be used even with telephone company central offices that are not equipped to do SMS over landline.

The user starts the transfer process by depressing the button on the meter 10 as shown in FIG. 2B. On-going data transfer may be indicated on the display of the meter 10, or as a light on the base station 11. The base station 11 later communicates the information to a remote site by means of the telephone 22. Successful communication may be indicated by illumination of a light on the base station.

Figure 3A:
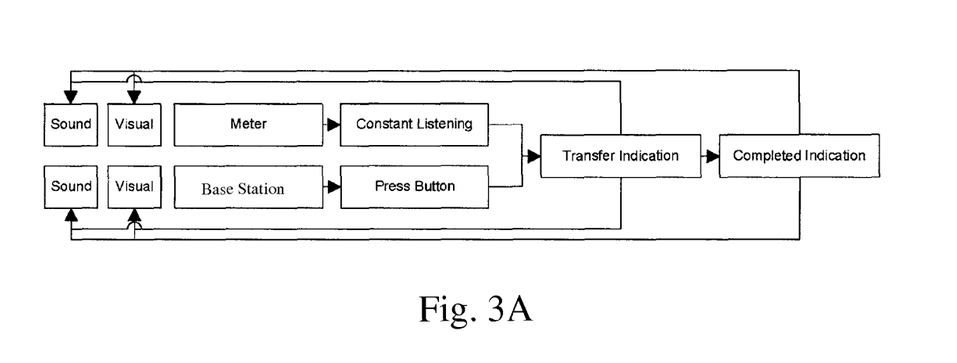
FIGS. 3A and B depict a sequence of steps using the pressing of a button on a base station to initiate the data collection system of the invention.

FIGS. 3A and B depict another method by which communication between the meter 10 and the base station 11 may be initiated. In this instance the meter 10 operates in constant listening mode, and the data transfer process is initiated by depressing a button on the base station as shown in the FIG. 3B. Otherwise, the operation is similar to that of the embodiment depicted in FIGS. 2A and B. Thus, the meter listens constantly for a wireless signal from the base station. Eventually the user presses a button on the base station. This prompts the base station to transmit a signal to the meter. This signal causes the base station and meter to establish a wireless connection. The base station collects information from the meter. An indication, audio or visual or both, is provided to let the user know that the information transfer is taking place. The base station later communicates the information to a remote site by means of the telephone line as shown in the figure.

Figure 4:
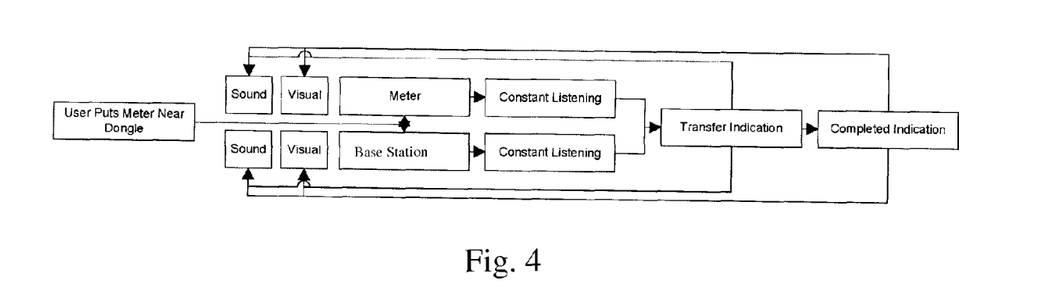
FIG. 4 depicts a sequence of steps using the placement of a meter nearby to a base station to initiate the data collection system of the invention.

FIG. 4 depict another method by which communication between the meter 10 and the base station 11 may be initiated. In this embodiment, the meter listens constantly for a wireless signal from the base station, and the base station listens constantly for a wireless signal from the meter. Eventually the user places the meter nearby to the base station. This proximity causes the base station and meter to establish a wireless connection. The base station collects information from the meter. An indication, audio or visual or both, is provided to let the user know that the information transfer is taking place. The base station later communicates the information to a remote site by means of the telephone line as shown in the figure. Successful communication is also indicated.

Figure 5A:
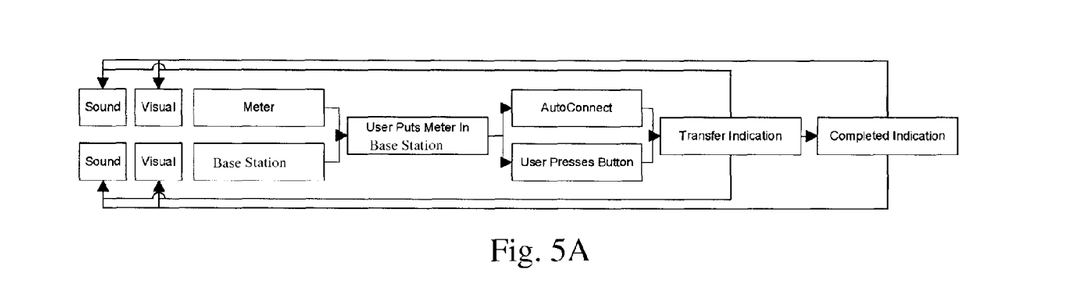
FIGS. 5A and B depict a sequence of steps using the insertion of a meter into a base station to initiate the data collection system of the invention.
Figure 5B:
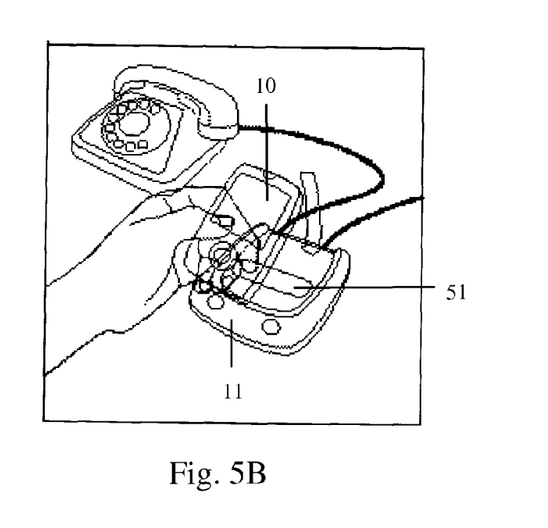

FIGS. 5A and B another method by which communication between the meter 10 and the base station 11 may be initiated. The user places the meter into a receptacle or docking location 51 in the base station 11. This event causes the base station and meter to establish an electrical connection. The establishment of the electrical connection can cause the data collection next described, or a press of a button on the meter by the user can cause the data collection next described. In either case, the base station collects information from the meter. An indication, audio or visual or both, is provided to let the user know that the information transfer is taking place. The base station later communicates the information to a remote site by means of the telephone line as shown in the figure. Successful communication is also indicated. If desired, the receptacle or docking location 51 in the base station 11 may also charge the battery of the meter.

Figure 6:
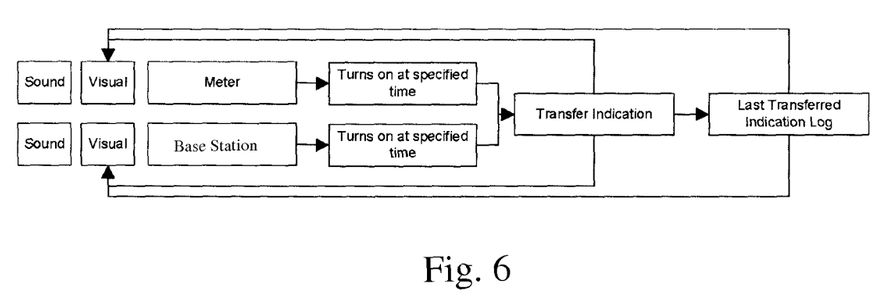
FIG. 6 depicts a sequence of steps triggered by the arrival of a specified time to initiate the data collection system of the invention.

FIG. 6 depicts another sequence of steps for initiation of the data collection protocol triggered by the arrival of a specified time. The meter and base station each keep track of the time of day, and at some predetermined time both the meter and base station prepare for a wireless communication. The meter may listen at that time for a wireless signal from the base station, in which case the base station sends a signal to the meter to initiate communications. Alternatively the base station may listen at that time for a wireless signal from the meter, in which case the meter sends a signal to the base station to initiate communications. In either case, what happens next is that the base station and meter establish a wireless connection. The base station collects information from the meter. An indication, audio or visual or both, may be provided to let the user know that the information transfer is taking place. The base station later communicates the information to a remote site by means of the telephone line as shown in the figure. Successful communication is also indicated.

As shown in the column below the meter in FIG. 1 and in the various methods for initiating data transfer, if the meter communication is wireless, this could be "continuous" in the sense that the meter could be prepared at all times to respond to a wireless signal, or could be prompted by a user input such as a button press at the meter. Alternatively, the wireless communication could be at a predetermined time of day or may occur without user intervention simply as a result of meter proximity to the base station. If the meter communication is wired at the means for communication, data transfer can be initiated as a consequence of the placement of the meter in the base station without further user intervention, or could be triggered by a user pressing a button on the meter after placement of the meter in the base station.

The base station has a similar range of options as shown in the second column of FIG. 1. If the base station communication is wireless, this could be "continuous" in the sense that the base station could be prepared at all times to respond to a wireless signal, or could be prompted by a user input such as a button press at the base station. Alternatively, the wireless communication could be at a predetermined time of day. It the base station communication with the meter is wired, data transfer can be initiated as a consequence of the placement of the meter in the base station without further user intervention, or could be triggered by a user pressing a button on the base station after placement of the meter in the base station.

Figure 3B:
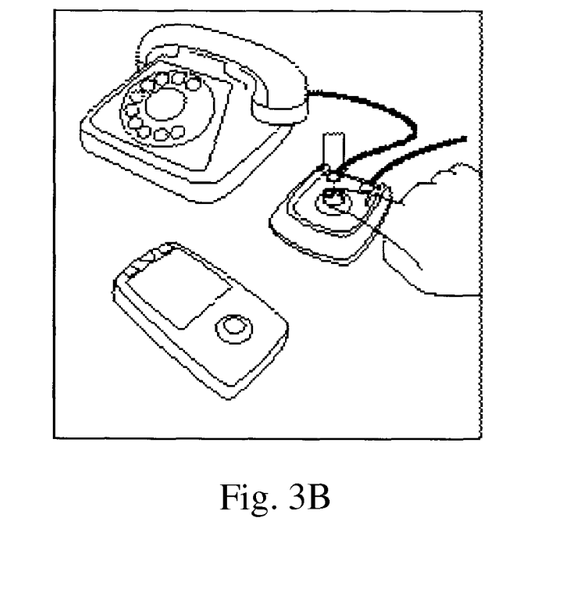

The approach of FIGS. 2a and 3 calls for the base station to listen constantly. This requires it to activate a wireless receiver constantly, which consumes some amount of electrical power. The base station, however, may be receiving power from an AC adaptor and may not be as constrained so far as weight is concerned so could have a larger battery than the battery in the meter.

Each of these approaches has some benefits and some drawbacks. Some call for the meter to listen constantly. This requires it to activate a wireless receiver constantly, which consumes some amount of electrical power. This may tend to use up the battery power in the meter, and thus is potentially a drawback.

The embodiment in which proximity alone is sufficient to initiate data transfer has the benefit that no user intervention is required, such that compliance monitoring is facilitated. It requires either that the meter listen constantly or that the meter listen constantly. The other of the two devices can simply "poll" its communications partner, and the "polling" happens only every now and then, and thus does not consume large amounts of electrical power. If the meter-listening-constantly approach is used, this tends to use up battery power in the meter, which is potentially a drawback. If the base station-listening-constantly approach is used, this tends to use up battery power in the base station, but the base station may have an external power source such as an AC adaptor, and in any event the weight constraints on the base station may not be as demanding as the weight constraints on the meter.

In the wired connection approaches, continuous wireless listening is not required from either the meter or the base station. Instead, the meter is able to be in a low-power mode if desired, until such time as it is placed into a receptacle on the base station. This minimizes power drain in the meter. This approach has the potential drawback, however, that connectors are needed and cost money. It also requires manipulating the meter into the docking station, which may be problematic if the system is being used under poor lighting conditions or by a user with limited vision or motor skills. Further, it requires a compliance action on the part of the user, namely placing the meter in the base station, which may be easily forgotten.

The time-base approach requires that both the meter and base station keep track of the time, so that communications may be established at that time. This requires some modest level of power consumption in the meter for timekeeping purposes. The rest of the meter, however, can be in low-power mode most of the time. If the meter and base station lose synchronization, for example due to drift in one of the clocks relative to the clock of the other device, then communications may be lost. Compliance with availability for data transfer can be facilitated by selecting a transfer time when the user is normally is a predictable location, such as home in bed.

A substantial advantage of the base station approach as described in the foregoing discussion is the ability to have multiple base stations disposed in different locations to facilitate transfer of data to the data receiving server 12. For example, a user may have one base station in the home, one at work or school, and another that travels with the user and can be plugged in even in a hotel room for communication to the data receiving server 12.

In addition, as noted above, the communication between the meter and the base station can be two way communication such that messages can be sent to the user and displayed on the meter. Examples of messages that can be transmitted in this way include, without limitation, (i) a warning of non-compliance with established test scheduled;

(ii) a recommendation to begin, cease or alter treatment regimens, (iii) a recommendation to alter the time at which self testing is done, and (iii) an alert that more consumables for use with the test meter are needed.

Such messages can be originated in the base station, or the data receiving server, or another computer connected to the depending on the nature of the message and the location of data evaluation.

Data Collection Interface of the Invention

In addition to improvement in the mechanism for initiating data transfer from a glucose or other analyte meter, the present invention also provide a data collection interface that can be used independently or together with the data collection system described above. In this case, the base station 11 may be a separate unit from the data receiving server 12 as depicted above, or they may be integrated. In general, the data receiving server 12 in this instance is desirably at a location frequented by the user since one purpose of the data collection interface of the invention is to facilitate the user's understanding of the data and management of the meter.

The interface in accordance with the present invention is a combination of a meter and a computer which exchanges data either directly or through a separate base station with the meter, and is embodied in the programming of the meter and/or the computer to provide one or more of the following functions:

(a) automatic launch of data transfer and result display programs upon connection of the meter with the computer.

(b) linking of data transferred from the meter with stored data for a user based on recognition of the serial number of the meter or other user identification provided from the meter, and displaying of combined data from a data management system of the new and previously stored data for the user.

(c) retrieval of the meter configuration and presentation of the configuration on a display associated with the computer that is not the meter display in the same format as the meter display, (d) retrieval of the meter configuration and presentation of the configuration on a display associated with the computer that is not the meter display in the same format as the meter display, and updating of the meter to incorporate configuration changes entered via the computer rather than via the meter.

Figure 7:
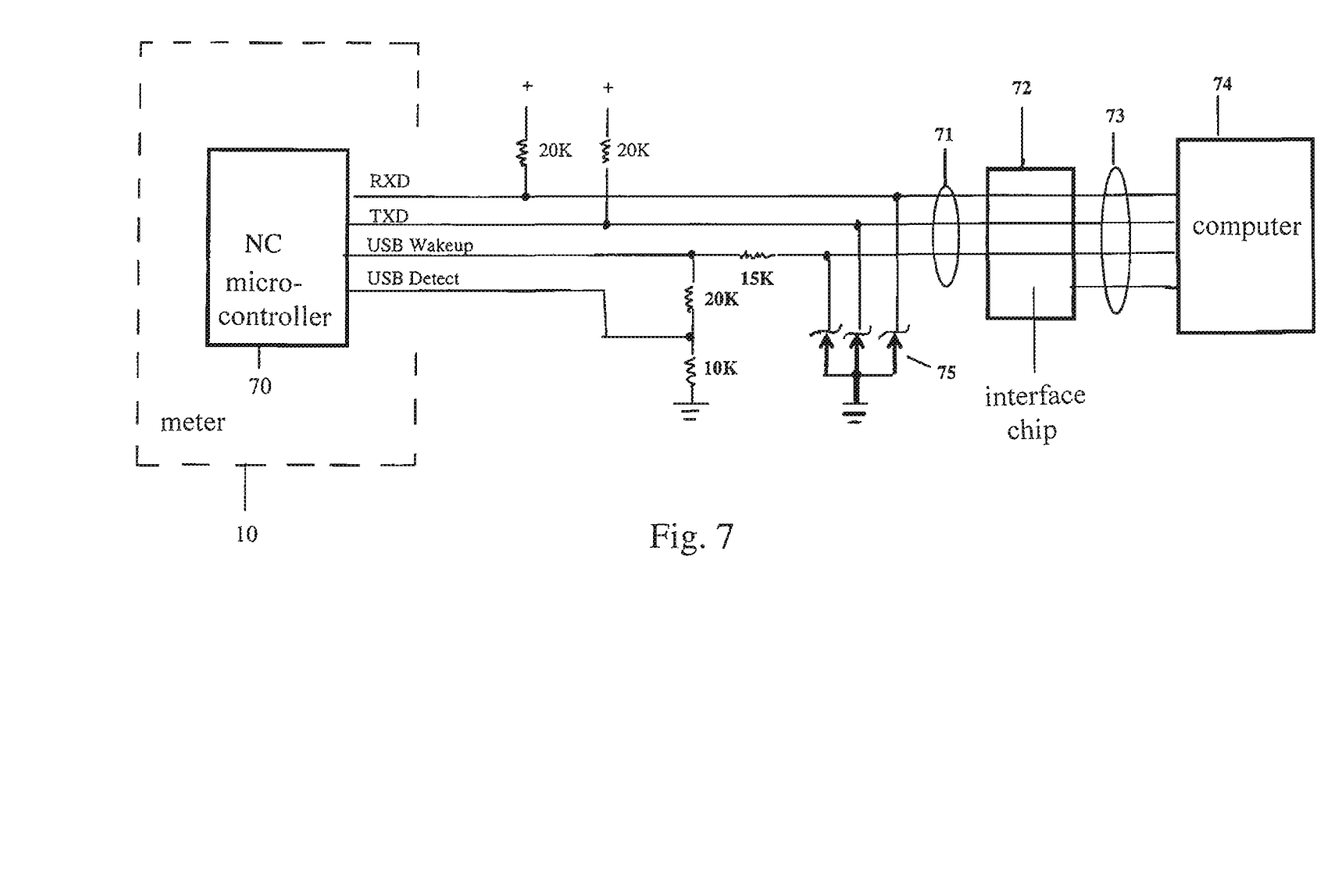
FIG. 7 shows some of the physical-layer connections that may exits between a meter and a computer.

FIG. 7 shows some of the physical-layer connections that may exits between a meter 10 and a computer 74. The meter 10 contains a microcontroller 70. In this embodiment, serial lines RXD and TXD pass between the microcontroller 70 and an interface chip 72. For example this can be by means of a serial cable 71. Optional diodes 75 help to protect against ESD (electrostatic discharge). Interface chip 72 can be a Silicon Laboratories CP2 102. The chip 72 provides a serial interface to connect with the microcontroller 70, and provides a USB interface to connect via USB cable 73 to a computer 74. The microcontroller 70 may have a UART built in (e.g. an equivalent pf an 8042) and the chip 72 has a UART interface.

Analytical circuitry, omitted for clarity in FIG. 7, permits the microcontroller 70 to connect to a test cell, such as an electrochemical test cell, to measure blood glucose or other analyte of interest. Circuitry suitable for this purpose is described in detail in U.S. application Ser. No. 10/907,790, filed Apr. 15, 2005, which application is incorporated herein by reference for all purposes.

It should be appreciated that the allocation of circuitry need not be exactly as is shown in FIG. 7. For example in FIG. 7 the chip 72 is in the middle of a cable which connects to the microcontroller 70 and to the computer 74. But in a different physical arrangement the chip 72 and microcontroller 70 could be in the same housing. In yet a different arrangement the microcontroller 70 could have a USB interface built in.

Figure 8:
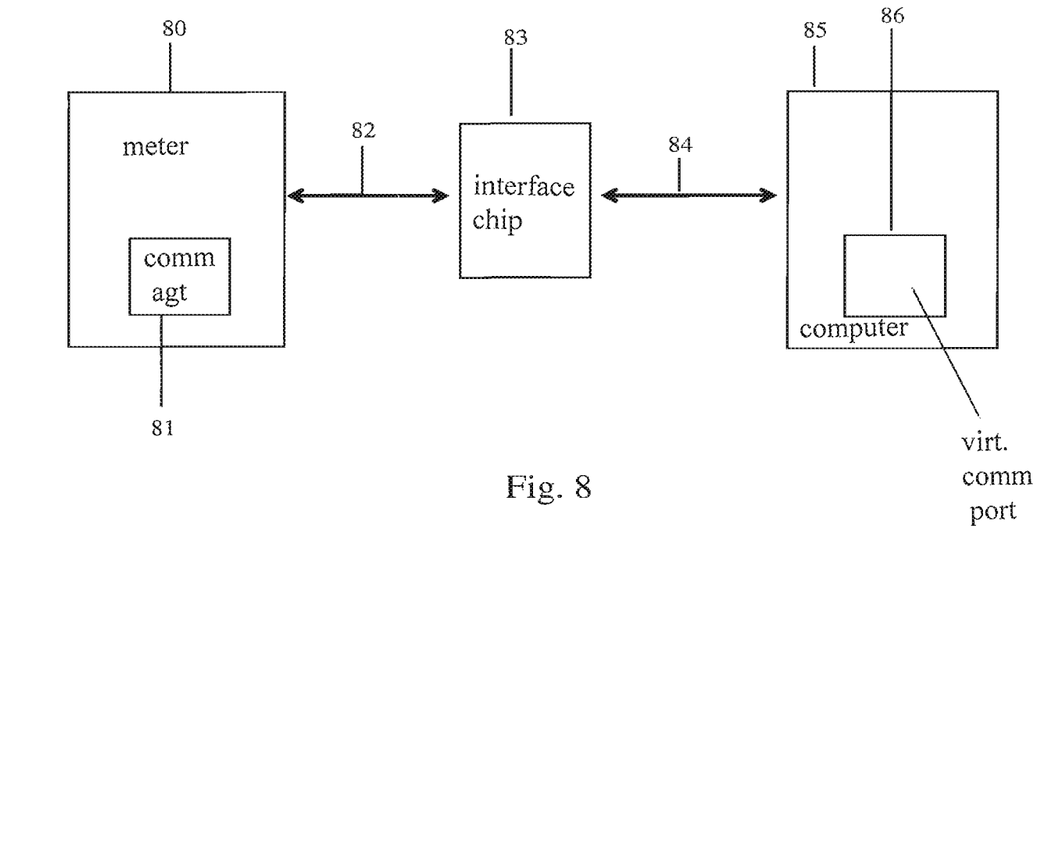
FIG. 8 is a higher-level functional block diagram as compared with FIG. 7

FIG. 8 is a higher-level functional block diagram as compared with FIG. 7. Meter 80 may be seen, which contains communication agent 81. A computer 85 may be seen, which contains a virtual communications port 86. Between these two devices is a cable 82, 83, 84. The cable 82 in this arrangement is a serial cable, and the cable 84 in this arrangement is a USB cable. Equipment 83 is a UART-to-USB interface chip as mentioned above.

The virtual communications port 86 may be provided by means of a suitable driver installed into the operating system. The chip 72 is powered through the USB port of the computer 74, 85, in a typical embodiment drawing 26 milliamperes.

The virtual communications port will be described in more detail. The maker of the chip 72 provides a driver for use in a Windows personal computer. The driver allows communication and detection by an operating system. When the sensed device (the chip 72) is detected by the hardware and by the operating system, an entry is made in the Windows system registry. (Similar device driver approaches may be used with other operating systems such as Mac or Linux.)

Also installed in the computer 74 or 85 is a meter agent. This is an application service that runs in the background of the operating system and detects the connection of the USB meter cable 82, 83, 84. Once the cable 82, 83, 84 is detected, the meter agent checks to see if a meter 80 is connected. The meter agent then proceeds to launch the user application (discussed below) in "Download" mode. This meter agent may, for example, be built from a standard Service Agent developer included with Visual Basic.NET (part of Visual Studio.NET 2003).

Also installed in the computer 74 or 85 is the user application. The user application is the main application where users can download and view reports of the readings they have downloaded from the meter, or that they have entered manually. The application is launched in "Regular" mode when the user clicks on the application shortcut. During this load cycle, it loads the application with default patient information first.

The application can be launched from the meter agent in "Download" mode. This mode will launch the application and begin to immediately download the reading from the connected meter. The application will change the startup profile to match the patient associated with the connected meter. The application may be developed using Visual Basic.NET (part of Visual Studio 2003) and may be based totally on the Microsoft NET framework.

Figure 9:
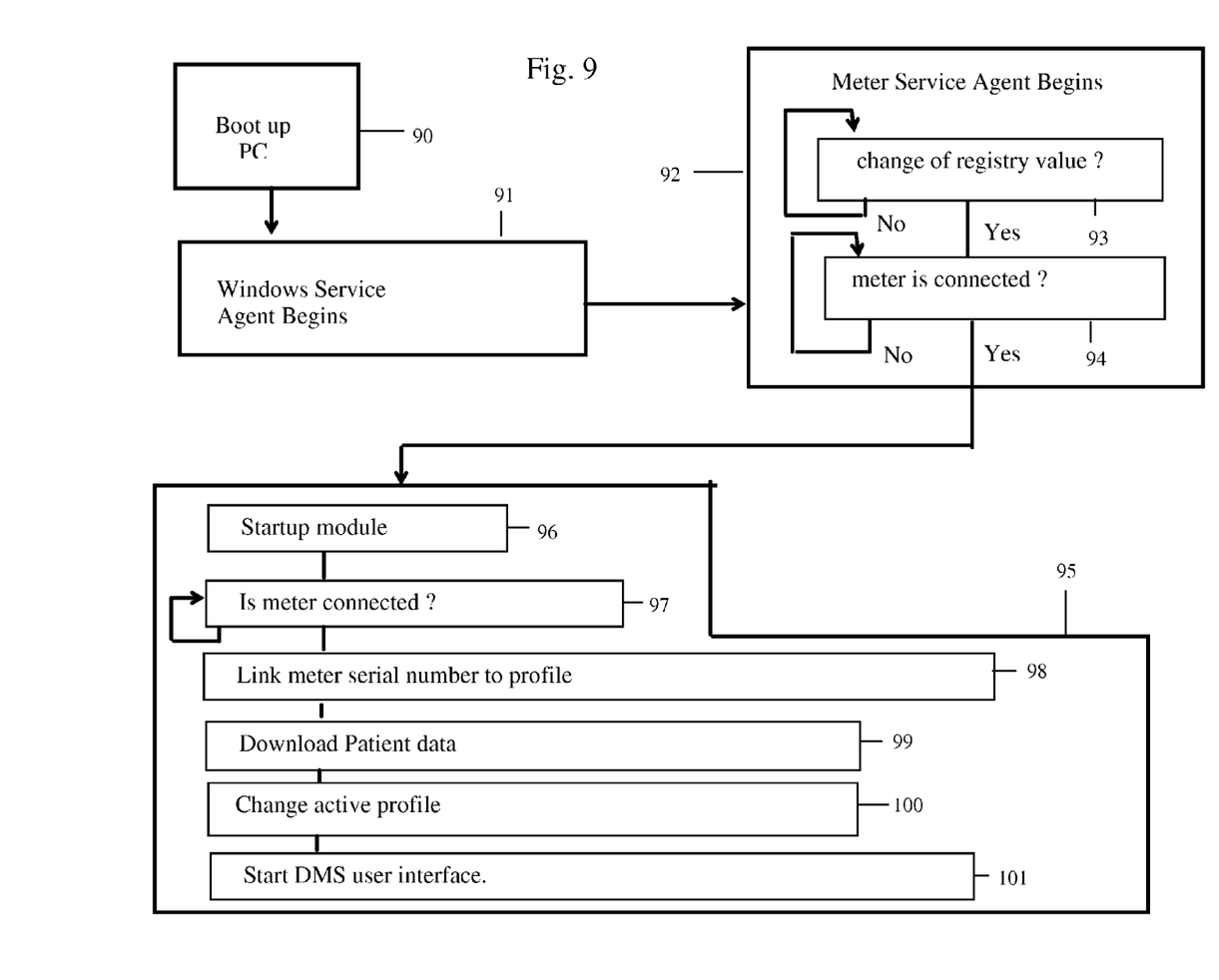
FIG. 9 shows a process flow for the interface according to the invention.

FIG. 9 shows a process flow for the interface according to the invention. First the personal computer boots 90. Then the windows service agent begins at 91. The meter service agent polls a registry value (at 93) to check to see whether the registry value has changed that would reveal that the USB cable and USB interface chip 72 has been detected.

If and when the registry value change is found, then flow proceeds to 94 where the meter service agent polls the cable to find out if a meter is connected to the cable. Eventually a meter is detected and process flow proceeds to 95, the database management system. Within this system, there is a startup module 96, followed by yet another test to make sure that the meter is still connected, at 97. If and when the meter is detected, then the meter is interrogated to learn an identifying indicium such as the serial number of the meter. This permits the system to link the subsequent steps, including data downloads, to a particular profile associated with that serial number, all at 98.

Next, in an automated way, patient data is downloaded from the meter to the user application within the computer, at 99. This can, for example be accomplished via the data collection system described above.

If the active profile was not already the profile associated with the detected serial number or other indicium, then the particular profile is designated as the active profile, at 100. Then the database management system user interface is launched, at 101.

It is instructive to describe what all of this looks like from the point of view of a human user. In this simple and streamlined process, the user starts up the application by plugging a device (the glucose meter, in this example) into a USB port. As soon as the device is plugged in, the associated application is launched, patient data is downloaded and/or synchronized, and results are automatically displayed. This sequence of events takes place without a requirement of any other user interaction with the computer.

In addition to launching because of the user connecting the meter, the main program (the user application) may start up at the user's initiative in either of two other ways. One way is to open the program by clicking on a desktop icon on the computer. The other way is to launch the user application with a suitable startup parameter set. In that mode, the user application searches for and detects the USB device, searches for and detects the meter, and downloads and/or synchronizes data and displays results when done.

Again, as mentioned above, a service agent detects the meter, and launches the user application in an auto-launch mode. Each profile or patient has a meter serial number associated with his or her profile. The application reads the serial number and works out which user profile matches that serial number. Downloaded data is then loaded into a database associated with that user profile.

Another aspect of the invention relates to the user interface of the meter itself, and to a depiction of that user interface (and indeed of the entire meter) on the screen of the connected personal computer. When the user application is running on the personal computer, one user option is to display a replica of the user interface of the meter. For example, a typical meter may have a liquid-crystal display screen and two or three buttons. When this user option is selected, what appears on the screen of the computer is a replica of that liquid-crystal display screen the buttons. The user application obtains from the meter all of the settings and internal states of the meter, and displays this on the computer screen. Any changes made on the computer screen (through the user application) can be changed on the meter. This propagation of changes from computer display to meter (or in the opposite direction) is preferably done in close to real time but is less preferably batched upon pushing an "update" button.

Several advantages present themselves given this aspect. A first advantage comes from the computer rendition of the display, which can be larger than the display on the meter itself. This permits the display to be easier to see (for those with limited visual acuity) and permits displaying more parameters simultaneously. The computer is able to have a larger memory and is able to perform "sanity checks" as to user inputs which a meter might not be able to perform. This feature of the invention can also be used to restore a "factory default" setting to the meter, or a patient-specific set of saved parameters. In this way, inadvertent or undesired changes to the meter's operating characteristics can be quickly and easily fixed.

This same display on the computer screen, when no meter is attached, can serve as a learning tutorial to learn the user interface of the meter. The user can press the (virtual) buttons on the display, and changes will be simulated on the screen.

What is claimed is:

1. A combination of an analyte detection meter and a data receiving server wherein the data receiving server exchanges data through a separate base station with the meter, wherein the meter and/or the data receiving server are programmed to provide one or more of the following functions:
    (a) automatic launch of data transfer and result display programs upon connection of the meter with the data receiving server
    (b) linking of data transferred from the meter with stored data for a user based on recognition of the serial number of the meter or other user identification provided from the meter, and displaying of combined data from a data management system of the new and previously stored data for the user
    (c) retrieval of the meter configuration and presentation of the configuration on a display associated with the computer that is not the meter display in the same format as the meter display, and
    (d) retrieval of the meter configuration and presentation of the configuration on a display associated with the data receiving server that is not the meter display in the same format as the meter display, and updating of the meter to incorporate configuration changes entered via the computer rather than via the meter, wherein the base station is operatively connected to the meter to transfer analyte data from the meter in response to a defined stimulus, said base station comprising means for communicating transferred analyte data to the data receiving server, and wherein the defined stimulus is the proximity of the meter to the base station such that a wireless signal from the meter can be detected by the base station and vice versa, whereby when the meter and the base station are in a predefined proximity analyte data transfer between the meter and the base station occurs in the absence of user intervention, other than a user bringing the meter into the predefined proximity to the base station.

2. The combination of claim 1, wherein the operative connection between the meter and the base station to transfer analyte data is a wireless connection.

3. The combination of claim 1, wherein the base station is in a separate housing from the data receiving server and has no mechanism for displaying results to a user.

4. The combination of claim 1, wherein the computer receives data from the base station and analyzes the data to transmit to a remote location at least one type of message selected from the group consisting of:
    (1) a message based on the number of tests done indicating that additional supplies may be needed by the user;
    (2) a message that the number or frequency of tests performed is not in compliance with monitoring needs of the user, and
    (3) a message that the numerical values of the test results is greater or less than a target value such that medial attention may be necessary.

5. The combination of claim 1, wherein base station further comprises means for communicating transferred data to the meter, and the meter comprises means for receiving the data.

6. The combination of claim 1, wherein meter and/or the computer are programmed to provide
    automatic launch of data transfer and result display programs upon connection of the meter with the computer, and
    linking of data transferred from the meter with stored data for a user based on recognition of the serial number of the meter or other user identification provided from the meter, and displaying of combined data from a data management system of the new and previously stored data for the user.

7. The combination of claim 1, wherein meter and/or the computer are programmed to provide
    automatic launch of data transfer and result display programs upon connection of the meter with the computer, and
    retrieval of the meter configuration and presentation of the configuration on a display associated with the computer that is not the meter display in the same format as the meter display.

8. The combination of claim 1, wherein meter and/or the computer are programmed to provide
    automatic launch of data transfer and result display programs upon connection of the meter with the computer, and
    retrieval of the meter configuration and presentation of the configuration on a display associated with the computer that is not the meter display in the same format as the meter display, and updating of the meter to incorporate configuration changes entered via the computer rather than via the meter.

* * * * *